(12) United States Patent
Zamanzadeh et al.

(10) Patent No.: US 8,154,279 B1
(45) Date of Patent: *Apr. 10, 2012

(54) NON-DESTRUCTIVE TESTING APPARATUS FOR THE DETECTION OF GRAPHITIZATION OF IRON

(75) Inventors: Mehrooz Zamanzadeh, Pittsburgh, PA (US); Gordon Kirkwood, Pittsburgh, PA (US); Sam Scheinman, Pittsburgh, PA (US)

(73) Assignee: Matco Services, Inc., Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/800,503

(22) Filed: May 17, 2010

Related U.S. Application Data

(63) Continuation of application No. 12/074,153, filed on Feb. 29, 2008, now Pat. No. 7,719,266.

(51) Int. Cl.
*G01N 27/82* (2006.01)
(52) U.S. Cl. ......................... 324/240; 324/228
(58) Field of Classification Search ................. 324/228, 324/237–238, 240–242
See application file for complete search history.

(56) References Cited

U.S. PATENT DOCUMENTS

| | | | | |
|---|---|---|---|---|
| 4,096,437 A | * | 6/1978 | Kitzinger et al. | 324/227 |
| 4,247,818 A | * | 1/1981 | Hiroshima et al. | 324/202 |
| 4,909,091 A | * | 3/1990 | Ellmann et al. | 73/866.5 |
| 5,030,911 A | * | 7/1991 | Lam | 324/226 |
| RE40,166 E | | 3/2008 | Sukhorukov et al. | |
| 2003/0011363 A1 | * | 1/2003 | Wayman et al. | 324/238 |
| 2004/0189289 A1 | | 9/2004 | Atherton | |
| 2011/0057649 A1 | * | 3/2011 | Yoshida et al. | 324/210 |

OTHER PUBLICATIONS

"Gray Iron—A Unique Engineering Material," by D.E. Krause,Gray,Ductile and Malleable Iron Castings-Current Capabilities, ASTM STP 455,Philadelphia,Pennsylvania, ASTM:1969, p. 3.
"Development of a Cast Iron Graphitization Measurement Device," NYGAS Technology Briefs, Issue 99-690-1, Jan. 1999.
"Electromagnetics: History, Theory and Applications" by R.S. Elliott, The Institute of Electrical and Electronics Engineers, New York, New York, 1993, p. 412.
"Case Histories of Failures in Water Mains," by M. Zamanzadeh et al., Corrosion/90, Paper No. 389 Houston, Texas: NACE, 1990.

* cited by examiner

*Primary Examiner* — Bot Ledynh
(74) *Attorney, Agent, or Firm* — Price & Adams

(57) ABSTRACT

A sensor measures the interaction of an applied magnetic field to an iron sample surface to determine whether the sample surface has been graphitized. The sensor measures the magnetic force resulting from the interaction or the magnetic flux density to determine the content of magnetic material in localized regions of the sample surface. The sensor includes a cantilever beam with a strain gauge for measuring magnetic force. Alternatively, the sensor includes a magnetic flux density sensor to measure magnetic flux density.

20 Claims, 5 Drawing Sheets

FLUX-BASED MEASUREMENT ON GRAPHITE INSERT PLATE
HALL-EFFECT WAND SENSOR PLACED IN CONTACT WITH SAMPLE

NON-DESTRUCTIVE TESTING APPARATUS FOR THE DETECTION OF GRAPHITIZATION OF IRON

CROSS-REFERENCE TO RELATED APPLICATIONS

This application is a continuation of U.S. patent application Ser. No. 12/074,153 filed on Feb. 29, 2008 now U.S. Pat. No. 7,719,266. The disclosure of the above application is incorporated herein by reference.

BACKGROUND OF THE INVENTION

1. Field of the Invention

This invention relates a method and apparatus for the sensing of magnetic properties and, more particularly, to a non-destructive testing device for detecting graphitization and localized corrosion in gray cast iron, ductile iron, ferrous alloys and other magnetic materials based on magnetic force or magnetic flux density measurements.

2. Description of the Related Art

Water main failures are very expensive for municipalities because they typically result in expenses associated with repair costs, flood damage, and loss of revenue to affected businesses. Water main failures also interrupt the operation of vital services, such as medical care and fire fighting operations. Currently, millions of dollars are spent annually by industry and by municipalities on the repair of failed components of the water distribution infrastructure, such as components that are made from gray cast iron or "gray iron" pipe.

The rate of municipal water main failure is expected to increase as the existing gray iron infrastructure continues to age. The cost of repairing damages caused by broken water mains (and subsequent flooding damage) may become an important item in many municipal budgets. The development of a non-destructive sensing technique to detect defects in the water distribution infrastructure to prevent catastrophic failure of water distribution infrastructure components would result in tremendous savings.

A non-destructive testing technique could be used in a program that is designed to detect localized corrosion before actual failures occur. A typical program would include identification of microstructure (gray iron, ductile iron, or other), identification of corrosion mechanisms, determination of the extent of internal and external corrosion (maximum and minimum wall thickness), determination of degradation and distribution of the magnetic properties of the metal, and an analysis of data and determination of preventative action. The monitoring of pipe corrosion would be continued for a few years beyond the application of corrosion control measures.

The metallurgy of gray iron is disclosed in detail in the publication entitled "Iron—A Unique Engineering Material," by D. E. Krause, *Gray, Ductile and Malleable Iron Castings—Current Capabilities*, ASTM STP 455, Philadelphia, Pa., ASTM: 1969, p. 3. The most important elements in gray iron, aside from iron, are carbon and silicon. The silicon content affects the carbon distribution in the metal.

Unlike the carbon in ductile iron and steel, which is disbursed as graphite spheroids and pearlite, respectively, the carbon in gray iron is present in flake form. These flakes form in the eutectic cell boundaries during cooling of the cast metal. The resulting graphite flakes form a continuous matrix throughout the gray iron.

A gray iron sample that includes an increased amount of silicon will have a decreased amount of carbon in the eutectic phase. Such a sample will have an increased amount of carbon in the form of pearlite and a decreased amount of graphite flakes. The lower content of graphite flakes results in an increase in tensile strength.

Typically, gray iron component failure is attributed to graphitic corrosion or graphitization. Graphitization occurs when the metallic constituents of gray iron are selectively removed or converted into corrosion products. Graphitization leaves behind the graphite matrix of the gray iron in the shape of the original casting. Graphitic corrosion is particularly insidious because graphitized pipe may appear perfectly sound upon visual inspection despite being embrittled and prone to premature failure under load.

Graphitic corrosion is one example of the dealloying of a metal. During dealloying, one component of an alloy is selectively dissolved, leaving other components behind. The preferential attack on iron in gray iron results from the fact that graphite is located at a highly noble or corrosion resistant position in the galvanic activity series. The relative position of two metals in the galvanic activity series determines which will most readily participate in electrochemical reactions, such as corrosion.

Pipes that are subject to graphitization may appear sound and may conduct water adequately. However, the metallic portion of a pipe wall may be significantly thinner in various places along the wall. Graphitized regions of the pipe wall will be brittle and subject to failure under load as the result of temperature variation, heavy traffic, or shock.

The galvanizing of iron with zinc inhibits corrosion because iron is nobler in the activity series than zinc. Therefore the zinc plating layer is preferentially attacked, greatly extending the service life of the iron substrate.

Similarly, graphite is far more noble than iron, so that the graphite matrix within the gray iron can act as the cathode in an electrochemical reaction under the right conditions of soil composition and moisture. The iron in gray iron samples that are subject to an electrochemical reaction will undergo anodic attack. In such samples, the graphite matrix will survive, while the iron is dissolved away.

The properties of iron that could be used to detect graphitization or other localized corrosion phenomena include ductility, electrical resistivity, or acoustic properties, such as ultrasonic sound velocity or attenuation. However, assessing ductility, by nature, involves destruction of the sample. Acoustical methods cannot be used with coated pipes due to the fact that it requires surface contact with bare, clean metal.

The publication entitled "Development of a Cast Iron Graphitization Measurement Device," NYGAS Technology Briefs, Issue 99-690-1, January 1999, discloses a meter that uses eddy currents to measure the electrical resistivity of a sample surface. Eddy current methods require sophisticated control circuitry and precisely tuned components. The eddy current device necessarily consumes a considerable amount of power to generate the RF signal that it uses to induce eddy currents in the sample.

Ultrasonic measurement of acoustic properties requires a very clean interface between the probe and the pipe for purposes of acoustic transmission and impedance matching, so that it is poorly suited for use with exposed, buried pipe which is often wet or dirty. Accordingly, there is a need for an improved non-destructive testing method and apparatus for detecting the graphitization of gray iron.

SUMMARY OF THE INVENTION

In accordance with the present invention there is provided a non-destructive testing apparatus. A housing holds a sensor and a magnetic field generator. The generator generates a magnetic field to interact with an iron sample surface. The sensor-measures the interaction of the generator with the iron sample surface. A processor connects to the sensor. The processor receives measurements from the sensor and uses the measurements to determine the amount of graphitization that has occurred on the sample surface. The processor sends output corresponding to the amount of graphitization that has occurred on the sample surface to a display device.

Further in accordance with the present invention, there is provided a device for measuring the extent of graphitization of an iron sample that includes magnetic materials. Means is provided for generating a magnetic field to interact with the iron sample surface. Means is provided for sensing the interaction of the magnetic field with the sample surface along the iron sample surface. Means is provided for comparing the interaction of the magnetic field with the iron sample surface to a calibration standard to determine the amount of graphitization that has occurred on the iron sample surface and to send graphitization measurement output to a display device.

Further in accordance with the present invention, there is provided a method for detecting the graphitization of an iron sample surface. A magnetic field is applied to a sample surface. The interaction of the magnetic field with the sample surface is measured to obtain an interaction value from the sample surface. The interaction of the magnetic field with the iron sample surface is compared to a calibration standard within a memory device to determine the amount of graphitization that has occurred on the iron sample surface. Output relating to the amount of graphitization that has occurred on the iron sample surface from the memory device is sent to a display device.

Accordingly, a principal object of the present invention is to provide a non-destructive testing device that measures graphitization in gray iron, ductile cast iron, ferrous alloys, and other magnetic materials.

Another object of the present invention is to provide a non-destructive testing apparatus that measures the interaction of a magnetic field generator with an iron sample surface.

Another object of the present invention is to provide a testing apparatus for measuring the magnetic force or magnetic flux density generated by a magnet in close proximity to an iron sample surface.

A further object of the present invention is to provide a non-destructive testing device for preventing water main failures.

These and other objects of the present invention will be more completely described and disclosed in the following specification, accompanying drawings, and appended claims.

DESCRIPTION OF THE PREFERRED EMBODIMENTS

The present invention is employed with non-destructive testing devices that rely upon measurements of the interaction of magnetic fields with sample surfaces that include magnetic materials. The term "magnetic materials" should be understood to mean materials having ferromagnetic and significant paramagnetic properties. The invention is particularly adapted for detecting graphitization of ferrous alloys, particularly gray iron or ductile iron. The invention is also suitable for detecting other types of localized corrosion phenomena in such samples, as well as localized corrosion phenomena in other materials that include magnetic components.

The non-destructive testing devices use the magnetic properties of the sample material to determine the homogeneity of regions of the sample surface. Magnetic properties, such as magnetic permeability, magnetic force, and magnetic flux density, provide such devices with the ability to detect graphitic corrosion on gray iron sample surfaces.

Magnetic permeability delivers highly localized measurements and is vastly more tolerant than electrical or acoustic methods with respect to surface preparation. The property of "permeability" is denoted by the Greek character $\mu$ and is a measure of how easily magnetic fields will penetrate a material. The publication entitled "Electromagnetics: History, Theory and Applications" by R. S. Elliott, The Institute of Electrical and Electronics Engineers, New York, N.Y., 1993, p. 412, discloses that the "relative permeability" of a material, $\mu r$, refers to the permeability of the material relative to that of free space in dimensionless units.

The relative permeability with respect to magnetic fields is essentially analogous to electrical conductance with respect to electric current. Since the electrical conductance is the reciprocal of resistance, 1/R, the greater the conductance, the easier it is for currents to flow in a material. Similarly, magnetic fields more readily pass through materials having higher values of $\mu r$.

All (non-superconducting) materials possess a resistivity greater than zero, so that inserting an additional length of any material into a circuit can only serve to reduce total conductance (1/R), because the newly added material introduces more resistance (R).

The relative permeability of a material is not constrained this way. For example, diamagnetic materials may have a relative permeability that is less than zero. The analogy would be to a material with negative conductance, which produces currents opposed to applied voltage.

Ferromagnetic materials become strongly polarized in the direction of an applied field in contrast to diamagnetic materials, which oppose applied magnetic fields. Due to the magnetization of the ferromagnetic material, the field strength near the material surface is actually increased above that of the applied field in free space.

Figure 1:
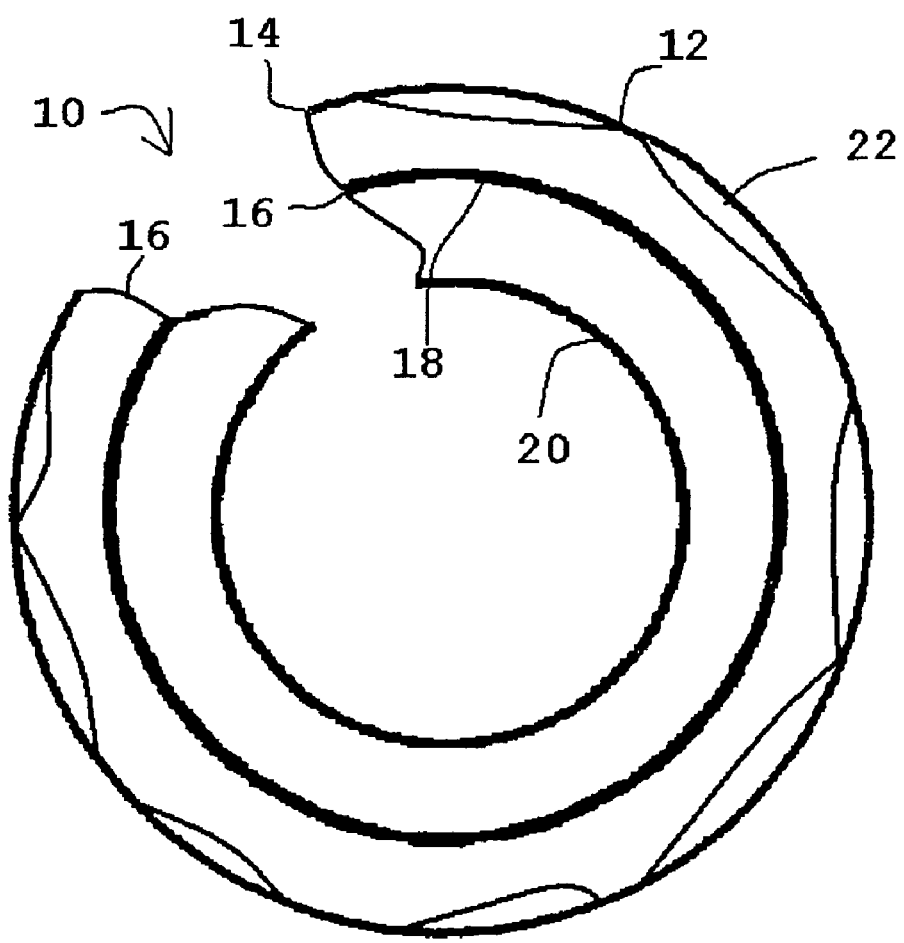
FIG. 1 is an elevational view of the cross section of a graphitized pipe sample.
Figure 2:
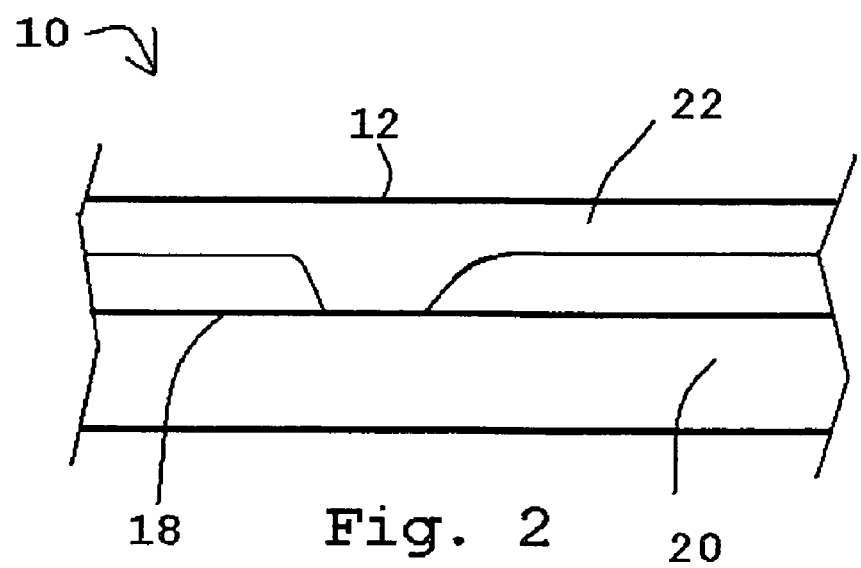
FIG. 2 is a fragmentary elevational view of the cross section of the graphitized pipe sample shown in FIG. 1.

Referring to the drawings and, particularly, to FIGS. 1 and 2, there is illustrated a graphitized pipe generally designated by the numeral 10. The graphitized pipe 10 corresponds to the gray cast iron sample disclosed in publication entitled "Case Histories of Failures in Water Mains," by M. Zamanzadeh et al., *Corrosion/90*, Paper No. 389 Houston, Tex.: NACE, 1990.

The gray cast iron sample 10 was taken from a water main that fractured after being subjected to graphitization corrosion. Chemical analysis of the sample indicated the presence of carbon (3.11%), manganese (0.39%), phosphorus (0.39%), sulfur (0.073%), and silicon (1.59%) in quantities that met the chemical requirements for gray cast iron alloys that are used in pipe applications.

Visual inspection of the sample 10 revealed primary and secondary cracks on an outside surface 12 of the pipe sample 10. A crack 14 initiated at the outer surface 12 and propagated inward, resulting in a longitudinal fracture 16. The Brinell hardness of the pipe 10 was 83.5 HB. The hardness near the fracture 16 measured 82 HB. The pipe 10 met the Talbot test (modulus of rupture and secant modulus of elasticity) requirements for gray cast iron.

An inside surface 18 of the pipe 10 included a continuous cement coating 20. The coating 20 was strongly adherent to the surface 18 and did not include any evidence of corrosion. Micrographs revealed a carbon distribution consistent with ASTM standards for gray iron, with graphite, ferrite, and pearlite visible. The graphite was of ASTM A247 type B. The soil (not shown) above and below the failed pipe 10 had a measured resistivity of 1100 to 2300 ohm-cm.

Similar pipes that were used in under similar conditions experienced an increasing failure rate over time. This increase in failure rate is typical of a piping system undergoing corrosion. The failures could not be attributed to brittleness, alone, so that graphitization corrosion and wall thinning was suspected. The observed failures included longitudinal fractures that occurred when such pipes were subjected to a crushing load at locations weakened by graphitization.

Visual observation, optical microscopy, and EDS (energy dispersive x-ray spectroscopy for analysis of chemical composition) microanalysis showed localized corrosion 22 on the exterior surface 12 of the pipe 10. Examination of the internal surface 18 showed no signs of either localized or uniform corrosion. Metallographic examination of the cross section showed the characteristic appearance of localized graphitization 22 with 25% penetration of the pipe wall.

Figure 3:
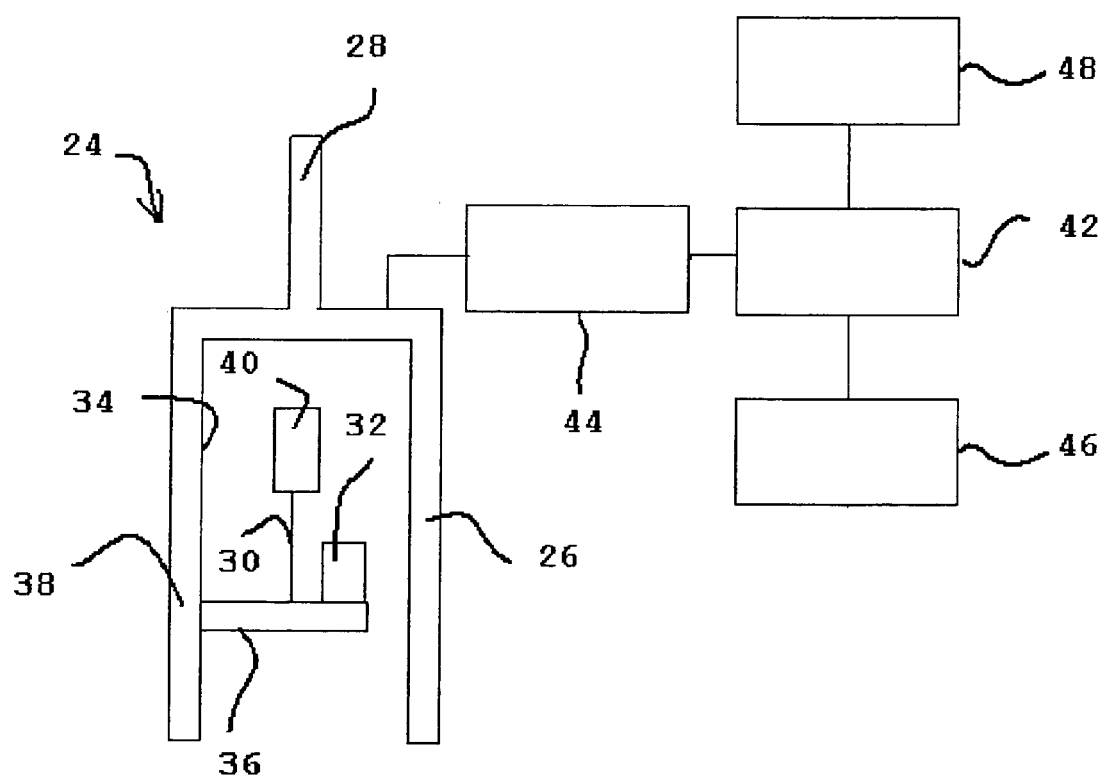
FIG. 3 is a schematic diagram of a non-destructive testing apparatus that measures magnetic force to determine the amount of graphitization in a sample surface.

Referring now to FIGS. 1-3, there is illustrated a non-destructive testing apparatus generally designated by the numeral 24 for determining the amount of graphitization or localized corrosion that has occurred in the sample 10. The apparatus 24 determines the amount of corrosion that has occurred in the iron sample 10 by measuring the magnetic force created by the interaction of a magnetic field with various regions of the sample 10.

Iron is selectively removed through corrosion in a typical sample surface 10. The corroded sample surface 10 includes graphitized areas 22 of gray iron that exhibit reduced magnetic permeability.

The difference in magnetic or relative permeability between intact iron and graphitized areas is used to measure the corrosion of iron at various locations along a sample surface 12. Graphite is a diamagnetic material because it has a relative permeability of −0.6. Iron is a ferromagnetic material. As iron is removed by dealloying and the ratio of iron to graphitized material decreases, the relative permeability of the material also decreases.

The ferromagnetic properties of iron cause an iron sample surface to exhibit high magnetization (magnetic polarization) and high permeability to applied fields. The relative permeability of a pure, non-heat-treated iron sample typically is greater than or equal to approximately 200. The relative permeability of an annealed iron sample typically exceeds 5,000.

As shown in FIG. 3, the apparatus 24 includes a tubular housing or wand 26 and a handle 28. The handle 28 extends from the housing 26 to facilitate manual manipulation of the apparatus 24 to allow the measurement of the corrosion by measuring relative permeability at various locations along the sample surface 12. The housing 26 holds a magnetic field generator or magnet 30 and a sensor 32 within an internal cavity 34.

The housing 26 and the handle 28 are made from any suitable materials by any suitable manufacturing process. Preferably, the housing 26 and the handle 28 are made from non-ferrous materials.

The magnetic field generator 30 includes any suitable magnetic field generating apparatus, such as a permanent magnet, that applies an external magnetic field to the iron sample surface 12. The magnet field generator 30 connects to the sensor 32 with a non-ferrous fastener. Preferably, the magnet 30 is a cylindrical rare-earth permanent magnet.

As shown in FIGS. 1-3, the generator 30 is positioned on the end of a rigid beam 36 that is pivotally connected to a wall 38 of the housing 26 forming a cantilever. The generator 30, the sensor 32, and the beam 36 are arranged within the cavity 34 to allow the generator 30 to interact with the sample surface 12 when the housing 26 is positioned in close proximity to the sample 10.

The interaction between the generator 30 and the sample surface 12 causes the beam 36 to deflect relative to the sample surface 12. The sensor 32 includes a strain gauge 40 that measures the deflection of the beam 36. The strain gauge 40 transmits the deflection measurements to a processor 42, which calculates the force of attraction between the generator 30 and the sample surface 10.

The processor 42 is a suitable microcontroller, laptop computer, personal computer, network computer, or other computing device. The processor 42 utilizes custom software to perform data collection, sensor monitoring, and user interface functions. The sensor 32 transfers measurement data to the processor 42 through an analog-to-digital converter (ADC) 44. Preferably, the processor 42 includes an internal memory device (not shown).

The processor 42 has the ability to receive input through a keypad or other input device 46. The processor 42 also has the ability to send output to a display device 48. The processor 42 converts the deflection measurements or the magnetic force measurements into a suitable data structure or form for output to the display device 48. Preferably, the display device 48 includes an LCD display for output.

The processor 42 receives data from the sensor 32. The data is displayed on the display device 48 in its raw form or is used to calculate the magnetic permeability of the sample 10 or other magnetic property data in appropriate units. The processor 42 sends the magnetic property data to the display device 48 for output and, optionally, to a storage device (not shown) for logging.

The apparatus 24 measures the interaction of the magnetic field with the sample surface 10 to obtain an interaction value from the sample surface 10. The interaction value is converted into a magnetic permeability value or to a suitable quality metric within the processor 42 or within an external memory device (not shown). The calculated value is sent from the processor 42 to a display device.

As illustrated in FIGS. 1-3, the handle 28 is used to move the housing 26 relative to the sample 10 to allow the sensor 32 to take measurements at a plurality of locations along the sensor surface 12. The processor 42 receives the measurements from the sensor 32 and uses the measurements to determine the magnetic permeability of the sample surface 12 at each location. Preferably, the processor 42 uses the magnetic permeability measurements to generate a map of the magnetic permeability for output to the display device 48.

The apparatus 24 obtains a magnetic permeability map by having the magnet 30 generate a magnetic field to interact with the gray iron sample 10. The interaction of the magnetic field with the sample surface 12 causes the beam 36 to pivot with respect to the housing wall 38. The strain gauge 40 measures the deflection of the beam 36 and transmits a deflection value to the processor 42. The processor 42 compares the deflection value to a set of values obtained from a calibration standard to generate magnetic permeability data for the iron sample surface 10. The processor 42 formats the magnetic permeability data for output to the display device 48.

The apparatus 24 is sensitive to orientation with respect to the sample surface 12. The apparatus 24 is also sensitive to the weight of the magnet 30 due to the fact that the weight of the magnet 30 will deflect the beam 36. The effect of the weight of the magnet 30 may be compounded by the effect of orientation. Preferably, a low-cost MEMS accelerometer (not shown) is incorporated into the apparatus 24 to provide electronic compensation for the effect of orientation or the weight of the magnet 30.

Figure 4:
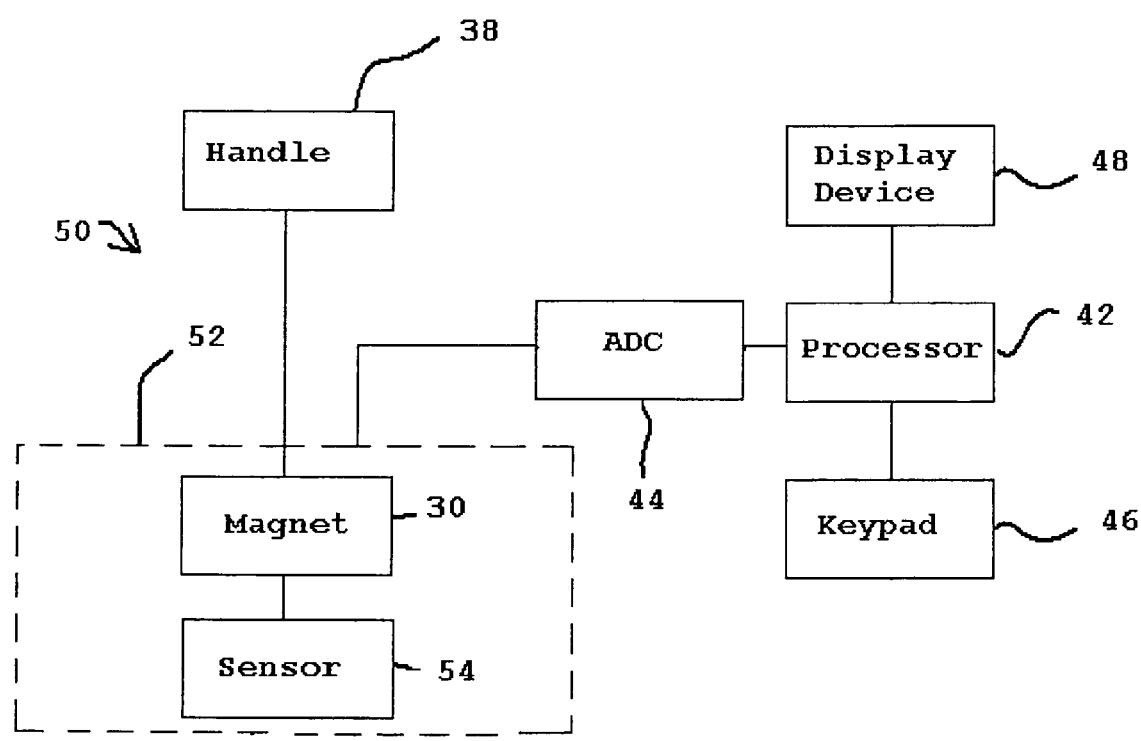
FIG. 4 is a schematic diagram of a non-destructive testing apparatus that measures magnetic flux density to determine the amount of graphitization in a sample surface.

Referring now to FIG. 4, there is shown a preferred embodiment of a non-destructive testing apparatus generally designated by the numeral 50 in which like elements are identified by like numerals shown in FIG. 3. The apparatus 50 measures the graphitization of the iron sample 10 shown in FIGS. 1-2 by measuring the magnetic flux density created by the interaction of a magnetic field with various regions of the sample surface 12. A lower flux density will be observed at the surface of a graphitized area 22 than at an intact iron surface due to the difference in permeability between graphitized and intact gray iron.

The testing apparatus 50 provides more direct measurements of permeability by determining magnetic flux density. Magnetic flux density correlates with graphitization because the decreased permeability in graphitized regions will result in lower flux density in those regions, as compared with intact regions. The magnetic flux density measurements are not sensitive to the orientation of the apparatus 50.

The apparatus 50 includes a handle 28 and a housing 52 extending from the handle 28. The housing 52 holds a magnetic field generator or magnet 30 that applies an external field to a sample and a suitable magnetic flux density sensor 54 that measures the flux density of the sample 10 shown in FIGS. 1 and 2.

Suitable magnetic flux density sensors include Hall effect sensors, giant magneto resistance (GMR) sensors, sense coils, pickup coils, optical sensors based upon the Faraday effect, and other flux density sensing sensors. Preferably, the sensor 54 is a Hall effect sensor that is affixed to the tip of housing 52 and is aligned with the pole of the magnet 30 in an orientation that facilitates measurement of the magnetic field parallel to the axis of the magnet 30.

The magnet 30 is positioned within the housing 52, so that there is an air gap of less than 1 cm when the sample surface 12 shown in FIGS. 1-2 contacts the housing 52.

As illustrated in FIG. 4, positioning the sensor 54 and the magnet 30 in close proximity to the iron sample 10 shown in FIG. 1 causes the magnetic flux to concentrate at the sample surface. The magnetic flux measurements that are obtained from this arrangement are superior because the field strength of the magnet 30 in free space diverges (and diminishes in strength) with increasing distance from the pole.

The processor 42 obtains field strength measurements from the sensor 54 that correlate with the amount of iron in the flux path. The field strength is higher over intact iron regions than over graphite-rich regions. The relationship is non-linear, so that the processor 42 generates output that uses terms such as "graphitization units", "corrosion severity", "iron depletion", or other such application-specific units for display on a linear scale on the display device 48.

The display device 48 also has the ability to display output using a generic "field strength" figure or other similar scales. This output allows a user to identify graphitized areas, as well as areas having below normal wall thickness due to other iron-removal mechanisms.

The apparatus 50 obtains a magnetic property map by having the magnet 30 generate a magnetic field to interact with the gray iron sample 10 shown in FIGS. 1-2. The Sensor 54 measures the interaction of the magnetic field with the sample surface 12 to determine the magnetic flux density at a location on the sample surface 12. The sensor 54 transmits a magnetic flux density value to the processor 42. The processor 42 compares the deflection value to a set of values obtained from a calibration standard to generate magnetic property data for the iron sample surface 12. The processor 42 formats the magnetic property data for output to the display device 48.

Figure 5:
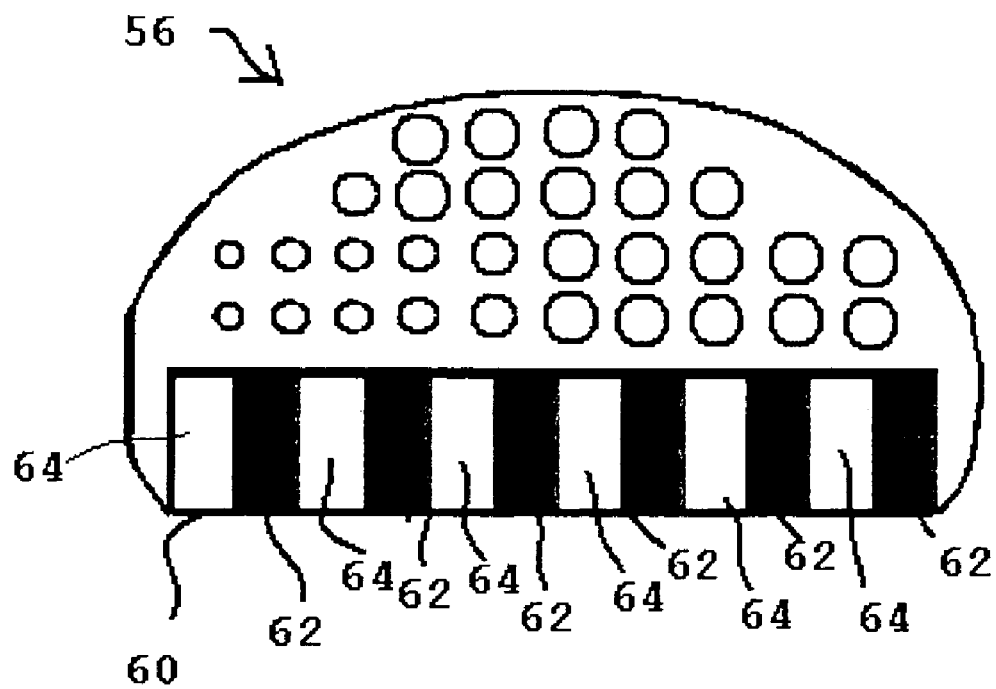
FIG. 5 is a plane view of a calibration sample that is used to calibrate the testing apparatus illustrated in FIG. 4.
Figure 6:
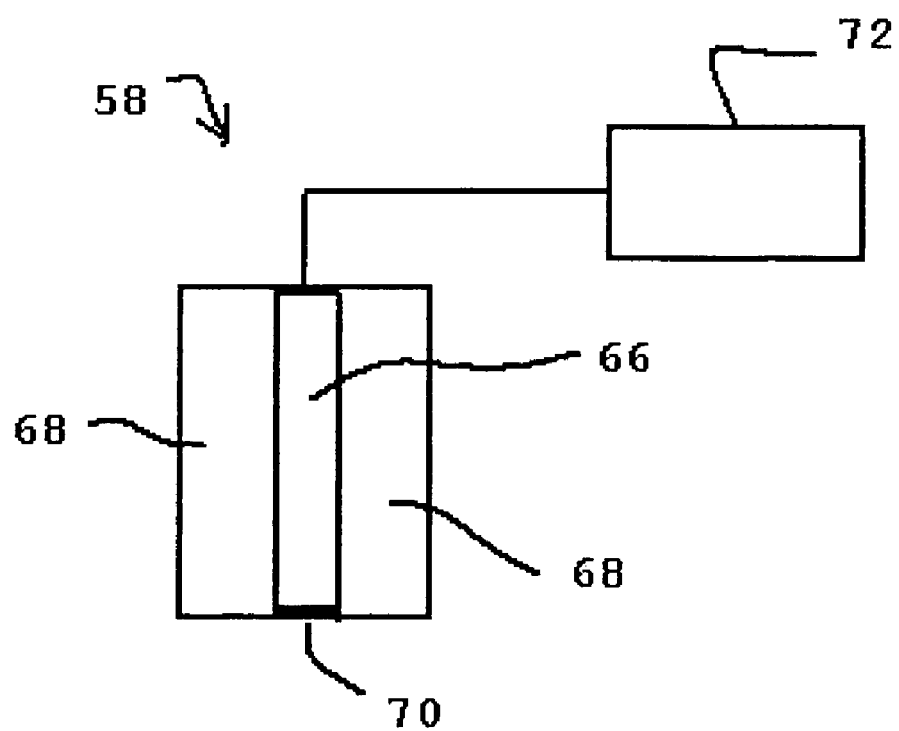
FIG. 6 is a schematic diagram of a prototype for the non-destructive testing apparatus shown in FIG. 4.

Referring now to FIGS. 5 and 6, there is illustrated a calibration standard generally designated by the numeral 56 that is used to test a prototype testing wand 58. The calibration standard 56 includes of a strip of gray iron plate 60, inlaid with a plurality of graphite strips 62, to define a plurality of gray iron regions 64. The graphite strips 62 progressively increase in thickness from one end to the other.

As shown in FIG. 6, the testing wand 58 includes a Sensor 66 positioned between a pair of nonferrous plates 68. The testing wand 54 has a flat tip 70 that presses against the iron regions 64 or the graphite strips 62 to measure field strength at various locations along the surface of the calibration standard 56. The testing wand tip 70 has a field strength of 122.3 G in free space.

The testing wand 58 connects to a gauss meter 72 that was manufactured by Alpha Labs of Salt Lake City, Utah. The gauss meter 72 generates output in voltage. The voltage measurements are converted into magnetic flux density measurements. It should be understood that the gauss meter 72 is intended for use with the testing wand 58 and not for use with the non-destructive testing devices 24, 50 shown in FIGS. 3-4.

Figure 7:
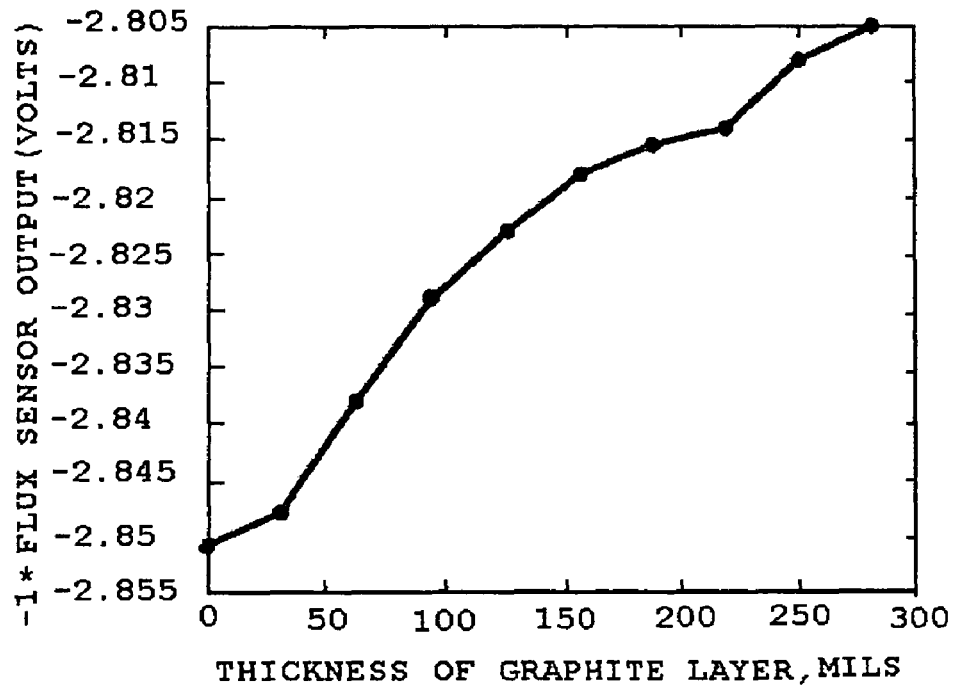
FIG. 7 is a plot of voltage output of a magnetic flux density sensor over graphite inserts of varying thickness.

Referring now to FIG. 7, the voltage output from the sensor 66 shown in FIG. 6 is illustrated. The voltage measurements are plotted as a function of graphite strip thickness. The graphite strip thickness ranged from 0 mils to 300 mils. The testing wand 58 utilizes a linear Hall effect sensor to obtain the voltage output, but the selection of a linear Hall effect sensor is not critical. Other magnetic flux density sensors are suitable.

The testing wand 58 obtained voltage readings that ranged from −2.85 Volts to −2.805 Volts. The voltage readings generally increased in a non-linear manner as the thickness of graphite increased, which demonstrates that magnetic flux density measurements decrease as a function of graphite strip thickness.

Figure 8:
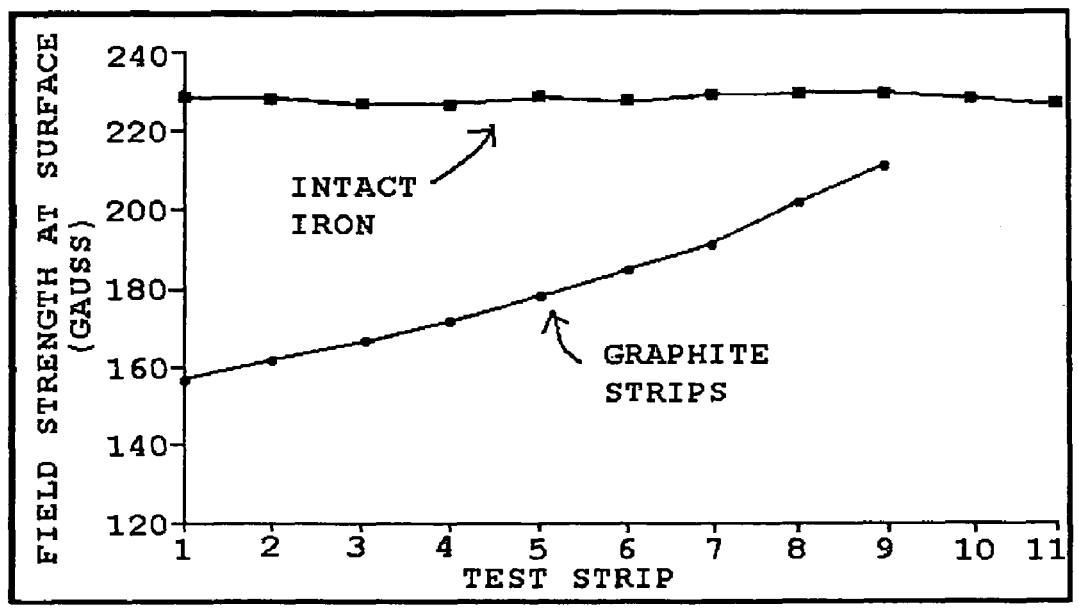
FIG. 8 is a plot of hand held graphitization sensor output.

Referring now to FIG. 8, the output from the testing wand 58 shown in FIG. 6 is graphically illustrated in magnetic flux density measurements. The output includes a set of measurements corresponding to a series of magnetic flux density measurements taken from a series of graphite strips 62 of varying thickness shown in FIG. 5. The magnetic flux density measurements, shown from left to right on FIG. 8, start with a measurement of 157.2 G for the thickest graphite strip to 210.9 G for the thinnest graphite strip.

The output also includes a set of magnetic flux density measurements taken at various points along an intact iron sample. The measurements remained essentially constant, ranging from 226.6 G and 229.5 G with a noise level of 0.6%.

It should be understood that, as an alternative to a single sensor, an array of sensors could be utilized in a non-destructive testing apparatus to facilitate the mapping of sample surfaces. The multiple sensors arranged in a pattern, such as a grid or plurality of concentric rings, are used to measure the gradient of magnetic field strength across a sample surface. Such sample surfaces have gradients of increasing field strength due to the presence of damaged regions and of intact regions.

It should also be understood that an alternate calibration standard is contemplated. The calibration standard includes inlaid strips of magnetite or hematite in place of the strips of graphite that are used in the calibration standard illustrated in FIG. 5. The alternative calibration standard is more difficult to manufacture, but provides a more accurate representation of the materials that are likely to be encountered in the field.

The alternate calibration standard is used to adjust various parameters to optimize sensitivity to the graphitized iron. The alternate calibration standard is used to optimize performance in evaluating iron thickness or thickness loss. The alternate calibration standard is also used to adjust magnet strength, magnet diameter, magnet distance from the magnetic flux density sensor, field sensor type (Hall, GMR, etc.), sensor gain, pre-amplifier gain, field focusing devices, and other similar parameters.

According to the provisions of the patent statutes, we have explained the principle, preferred construction and mode of operation of our invention and have illustrated and described what we now consider to represent its best embodiments. However, it should be understood that, within the scope of the appended claims, the invention may be practiced otherwise than as specifically illustrated and described.

We claim:

1. A non-destructive testing apparatus comprising:
    a housing holding a sensor and a magnetic field generator,
    said generator generating a magnetic field to interact with an iron sample surface,
    said sensor measuring the interaction of said generator with the iron sample surface,
    a processor connected to said sensor,
    said processor receiving measurements from said sensor and using the measurements to generate output in the form of magnetic permeability data representing the amount of graphitization that has occurred on the sample surface as output, and
    said processor formatting the magnetic permeability data corresponding to the amount of graphitization that has occurred on the sample surface to a display device.

2. A non-destructive testing apparatus as set forth in claim 1 in which:
    said generator generates a magnetic field for interacting with an iron sample selected from the group consisting of gray iron, gray cast iron, and ductile iron.

3. A non-destructive testing apparatus as set forth in claim 2 in which:
    said sensor includes a cantilever beam and a strain gauge,
    said strain gauge measures the deflection of said cantilever beam with respect to the iron sample surface to determine the amount of magnetic force from the interaction of said generator with the iron sample surface.

4. A non-destructive testing apparatus as set forth in claim 1 in which:
    said sensor measures magnetic flux density to measure the interaction of said generator with the iron sample surface.

5. A non-destructive testing apparatus as set forth in claim 4 in which:
    said sensor includes a flux density sensor.

6. A non-destructive testing apparatus as set forth in claim 1 which includes:
    said sensor and said magnetic field generator being in close proximity to the iron sample surface.

7. A non-destructive testing apparatus as set forth in claim 1 which includes:
    said magnetic field generator being a permanent magnet.

8. A non-destructive testing apparatus as set forth in claim 1 which includes:
    a handle connected to said housing.

9. A non-destructive testing apparatus as set forth in claim 1 which includes:
    a display device for receiving output from said processor.

10. A non-destructive testing apparatus as set forth in claim 1 which includes:
    said sensor measuring the interaction of the generator with the sample surface at a plurality of locations along the iron sample surface, and
    said processor receiving measurements from said sensor and using the measurements to generate a map of the graphitization of the iron sample surface for output to a display device.

11. A device for measuring the extent of graphitization of an iron sample that includes magnetic materials comprising:
    means for generating a magnetic field to interact with the iron sample surface,
    means for sensing the interaction of the magnetic field with the sample surface along the iron sample surface,
    means for comparing the interaction of the magnetic field with the iron sample surface to a calibration standard, and
    means for generating an output for display of magnetic permeability data corresponding to the amount of graphitization that has occurred on the iron sample surface and to send graphitization measurement output in the form of magnetic permeability data to a display device.

12. A device as set forth in claim 11 which includes:
    means for sensing the interaction of the magnetic field with the iron sample surface along the iron sample surface measuring magnetic force.

13. A device as set forth in claim 11 which includes:
    means for sensing the interaction of the magnetic field with the iron sample surface along the iron sample surface measuring magnetic flux density.

14. A device as set forth in claim 11 which includes:
    means for generating a magnetic field being in close proximity to the sample surface.

15. A device as set forth in claim 11 which includes:
    means for manipulating the device.

16. A device as set forth in claim 11 which includes:
    means for displaying the output.

17. A method for detecting the graphitization of an iron sample surface comprising:
    applying a magnetic field to a sample surface,
    measuring the interaction of the magnetic field with the sample surface to obtain an interaction value from the iron sample surface,
    comparing the interaction of the magnetic field with the iron sample surface to a calibration standard within a memory device to generate an output for display of magnetic permeability data corresponding to the amount of graphitization that has occurred on the iron sample surface, and sending output relating to the amount of graphitization that has occurred on the iron sample surface from the memory device to a display device.

18. A method as set forth in claim 17 which includes:
providing a housing having an internal wall and a cantilever beam pivotally connected to the internal wall,
positioning a magnet on the cantilever beam,
generating the magnetic field with a magnet positioned on the cantilever beam, and
measuring the deflection of a cantilever beam relative to the iron sample surface to determine the magnetic force between the iron sample surface and the magnet.

19. A method as set forth in claim 17 which includes:
generating the magnetic field with a magnet, and
measuring the magnetic flux density from the interaction of the magnet with the iron sample surface with a magnetic flux density sensor.

20. A method as set forth in claim 17 which includes:
measuring the interaction of the magnetic field with the sample surface at a plurality of locations to obtain a plurality of graphitization measurements to map the iron sample surface.

* * * * *